United States Patent [19]  
Nishiyama et al.

[11] 4,173,637  
[45] * Nov. 6, 1979

[54] N-BENZOYL-N'-PYRIDYLOXY PHENYL UREA AND INSECTICIDAL COMPOSITIONS THEREOF

[75] Inventors: Ryuzo Nishiyama, Takatsuki; Kanichi Fujikawa, Kusatsu; Rikuo Nasu, Kusatsu; Tadaaki Toki, Kusatsu, all of Japan; Toshihiko Yamamoto, deceased, late of Kusatsu, Japan; by Hikotaro Yamamoto, legal representative, Hyogo, Japan

[73] Assignee: Ishihara Sangyo Kaisha Ltd., Osaka, Japan

[*] Notice: The portion of the term of this patent subsequent to Nov. 6, 1996, has been disclaimed.

[21] Appl. No.: 899,461

[22] Filed: Apr. 24, 1978

Related U.S. Application Data

[63] Continuation-in-part of Ser. No. 844,174, Oct. 21, 1977.

[30] Foreign Application Priority Data

Oct. 29, 1976 [JP] Japan .................. 51-130903

[51] Int. Cl.² .................. A61K 31/44; C07D 213/64  
[52] U.S. Cl. .................. 424/263; 546/297; 546/300  
[58] Field of Search .................. 260/295 E; 424/263; 546/297, 300

[56] References Cited

U.S. PATENT DOCUMENTS 3,748,356  7/1973  Wellinga et al. .................. 260/295 E 4,005,223  1/1977  Sirrenberg et al. .................. 424/322

OTHER PUBLICATIONS

March, J., Advanced Organic Chemistry, McGraw-Hill, New York, 1968, pp. 672-673.

Primary Examiner—John M. Ford  
Assistant Examiner—Richard A. Schwartz  
Attorney, Agent, or Firm—Oblon, Fisher, Spivak, McClelland & Maier

[57] ABSTRACT

N-benzoyl N'-pyridyloxy phenyl urea having the formula

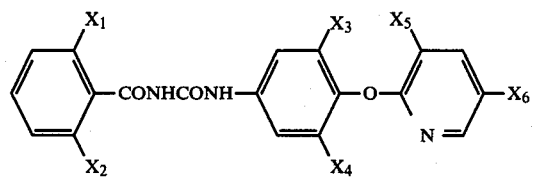

wherein $X_1$ represents a halogen atom or methyl group; $X_2$ represents hydrogen or halogen atom; $X_3$ and $X_4$ respectively represent hydrogen or halogen atom; $X_5$ represents hydrogen or halogen atom; and $X_6$ represents a halogen atom or nitro or trifluoromethyl group are novel compounds. The compositions containing the compound as the active ingredient are effective as the insecticide for extinction of injurious insects with high safety in agricultural, forestry and hygienic applications.

32 Claims, No Drawings

N-BENZOYL-N'-PYRIDYLOXY PHENYL UREA AND INSECTICIDAL COMPOSITIONS THEREOF

This application is a continuation-in-part of Ser. No. 844,174, filed Oct. 21, 1977.

BACKGROUND OF THE INVENTION

1. Field of the Invention:

The present invention relates to novel N-benzoyl N'-pyridyloxy phenyl ureas and the process for producing the same and the insecticidal composition containing the same.

2. Description of the Prior Arts

Almost of the conventional insecticides impart neurotoxicity and contact toxicity to all kinds of insects.

And, it has been required to find selective insecticidal compounds without toxicity to useful insects, N-benzoyl N'-phenyl ureas disclosed in U.S. Pat. No. 3,748,356 and N-benzoyl N'-phenoxyphenyl ureas (no pyridyloxy group) disclosed in U.S. Pat. No. 4,005,223 have such insecticidal properties.

The N-benzoyl N'-pyridyloxyphenyl ureas according to the present invention have a substantially better action than the above described known compounds.

SUMMARY OF THE INVENTION

It is an object of the present invention to provide novel N-benzoyl N'-pyridyloxy phenyl ureas.

It is another object of the present invention to provide a process for producing N-benzoyl N'-pyridyloxy phenyl ureas.

It is the other objects of the present invention to provide selective insecticidal compositions which are remarkably effective to certain injurious insects without affecting useful insects in remarkably low toxicity to animals.

The novel compounds of the present invention are N-benzoyl N'-pyridyloxy phenyl ureas having the formula

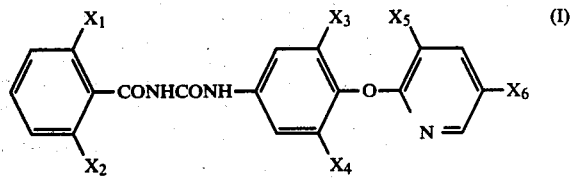

wherein $X_1$ represents a halogen atom or methyl group; $X_2$ represents hydrogen or halogen atom; $X_3$ and $X_4$ respectively represent hydrogen or halogen atom; $X_5$ represents hydrogen or halogen atom; and $X_6$ represents a halogen atom or nitro or trifluoromethyl group.

DESCRIPTION OF THE PREFERRED EMBODIMENTS

| Compound No. | Suitable compounds having the formula (I) include: |
|---|---|
| 1 | N-(2-chlorobenzoyl)N'-[3-chloro-4-(5-bromopyridyl-2-oxy)phenyl]urea m.p. 196° to 199° C. |
| 2 | N-(2-chlorobenzoyl)N'-[3-chloro-4-(5-nitropyridyl-2-oxy)phenyl]urea m.p. 209° to 212° C. |
| 3 | N-(2-chlorobenzoyl)N'-[4-(3,5-dibromopyridyl-2-oxy)phenyl]urea m.p. 185° to 188° C. |
| 4 | N-(2-chlorobenzoyl)N'-[3-chloro-4-(3,5-dibromopyridyl-2-oxy)phenyl]urea m.p. 223° to 224° C. |
| 5 | N-(2-chlorobenzoyl)N'-[4-(3,5-dichloropyridyl-2-oxy)phenyl]urea m.p. 216° to 218° C. |
| 6 | N-(2-chlorobenzoyl)N'-[3-chloro-4-(3,5-dichloropyridyl-2-oxy)phenyl]urea m.p. 225° to 228° C. |
| 7 | N-(2-chlorobenzoyl)N'-[3,5-dichloro-4-(3,5-dichloropyridyl-2-oxy)phenyl]urea m.p. 221° to 223° C. |
| 8 | N-(2-chlorobenzoyl)N'-[4-(5-bromopyridyl-2-oxy)phenyl]urea m.p. 179° to 180° C. |
| 9 | N-(2-chlorobenzoyl)N'-[3-chloro-4-(5-chlorpyridyl-2-oxy)phenyl]urea m.p. 198° to 200° C. |
| 10 | N-(2-chlorobenzoyl)N'-[3,5-dichloro-4-(5-chloropyridyl-2-oxy)phenyl]urea m.p. 147° to 148° C. |
| 11 | N-(2-chlorobenzoyl)N'-[4-(5-trifluoromethylpyridyl-2-oxy)phenyl]urea m.p. 149° to 151° C. |
| 12 | N-(2-chlorobenzoyl)N'-[3-chloro-4-(5-trifluoromethylpyridyl-2-oxy)phenyl]urea m.p. 182° to 185° C. |
| 13 | N-(2-chlorobenzoyl)N'-[4-(3-chloro-5-trifluoromethylpyridyl-2-oxy)phenyl]urea m.p. 186° to 187° C. |
| 14 | N-(2-chlorobenzoyl)N'-[3,5-dichloro-4-(5-trifluoromethylpyridyl-2-oxy)phenyl]urea m.p. 206° to 208° C. |
| 15 | N-(2-chlorobenzoyl)N'-[3,5-dichloro-4-(3-chloro-5-trifluoromethylpyridyl-2-oxy)phenyl]urea m.p. 140° to 144° C. |
| 16 | N-(2-chlorobenzoyl)N'-[3-chloro-4-(3-chloro-5-trifluoromethylpyridyl-2-oxy)phenyl]urea m.p. 224° to 226° C. |
| 17 | N-(2,6-dichlorobenzoyl)N'-[4-(3,5-dichloropyridyl-2-oxy)phenyl]urea m.p. 228° to 230° C. |
| 18 | N-(2,6-dichlorobenzoyl)N'-[3-chloro-4-dichloropyridyl-2-oxy)phenyl]urea m.p. 214° to 216° C. |
| 19 | N-(2,6-dichlorobenzoyl)N'-[3,5-dichloro-4-(3,5-dichloropyridyl-2-oxy)phenyl]urea m.p. 273° to 275° C. |
| 20 | N-(2,6-difluorobenzoyl)N'-[4-(3,5-dichloropyridyl-2-oxy)phenyl]urea m.p. 184° to 185° C. |
| 21 | N-(2,6-difluorobenzoyl)N'-[3-chloro-4-(3,5-dichloropyridyl-2-oxy)phenyl]urea m.p. 230° to 231° C. |
| 22 | N-(2,6-difluorobenzoyl)N'-[3-chloro-4-(5-chloropyridyl-2-oxy)phenyl] |

-continued

| Compound No. | Suitable compounds having the formula (I) include: |
|---|---|
| | urea m.p. 210° to 212° C. |
| 23 | N-(2,6-difluorobenzoyl)N'-[4-(5-trifluoromethylpyridyl-2-oxy)phenyl] urea m.p. 185° to 188° C. |
| 24 | N-(2,6-difluorobenzoyl)N'-[4-(3-chloro-5-trifluoromethylpyridyl-2-oxy) phenyl]urea m.p. 190° to 192° C. |
| 25 | N-(2,6-difluorobenzoyl)N'-[3-chloro-4-(5-trifluoromethylpyridyl-2-oxy) phenyl]urea m.p. 195° to 198° C. |
| 26 | N-(2,6-difluorobenzoyl)N'-[3,5-dichloro-4-(5-trifluoromethylpyridyl-2-oxy)phenyl]urea m.p. 209° to 212° C. |
| 27 | N-(2,6-difluorobenzoyl)N'-[3,5-dichloro-4-(3-chloro-5-trifluoromethylpyridyl-2-oxy)phenyl]urea m.p. 203° to 205° C. |
| 28 | N-(2,6-difluorobenzoyl)N'-[3-chloro-4-(3-chloro-5-trifluoromethylpyridyl-2-oxy)phenyl]urea m.p. 187° to 190° C. |
| 29 | N-(2-methylbenzoyl)N'-[4-(5-chloropyridyl-2-oxy)phenyl]urea m.p. 198° to 200° C. |
| 30 | N-(2-methylbenzoyl)N'-[4-(5-bromopyridyl-2-oxy)phenyl]urea m.p. 188° to 191° C. |
| 31 | N-(2-methylbenzoyl)N'-[4-(5-trifluoromethylpyridyl-2-oxy)phenyl]urea m.p. 140° to 142° C. |
| 32 | N-(2-methylbenzoyl)N'-[3-chloro-4-(5-bromopyridyl-2-oxy)phenyl]urea m.p. 207° to 209° C. |
| 33 | N-(2-methylbenzoyl)N'-[3-chloro-4-(5-trifluoromethylpyridyl-2-oxy) phenyl]urea m.p. 188° to 191° C. |
| 34 | N-(2-methylbenzoyl)N'-[3-chloro-4-(3,5-dichloropyridyl-2-oxy)phenyl] urea m.p. 213° to 215° C. |
| 35 | N-(2-methylbenzoyl)N'-[3,5-dichloro-4-(3-chloro-5-trifluoromethylpyridyl-2-oxy)phenyl]urea m.p. 214° to 217° C. |
| 36 | N-(2-methylbenzoyl)N'-[3-bromo-4-(3,5-dichloropyridyl-2-oxy)phenyl] urea m.p. 222° to 224° C. |
| 37 | N-(2-methylbenzoyl)N'-[4-(3,5-dichloropyridyl-2-oxy)phenyl]urea m.p. 216° to 219° C. |
| 38 | N-(2-methylbenzoyl)N'-[4-(3,5-dibromopyridyl-2-oxy)phenyl]urea m.p. 219° to 221° C. |
| 39 | N-(2-methylbenzoyl)N'-[4-(3-chloro-5-trifluoromethylpyridyl-2-oxy) phenyl]urea m.p. 171° to 173° C. |
| 40 | N-(2-methylbenzoyl)N'-[3,5-dichloro-4-(5-trifluoromethylpyridyl-2-oxy) phenyl]urea m.p. 219° to 221° C. |
| 41 | N-(2-methylbenzoyl)N'-[3-chloro-4-(3-chloro-5-trifluoromethylpyridyl-2-oxy)phenyl]urea m.p. 156° to 159° C. |

The N-benzoyl N'-pyridyloxy phenyl ureas having the formula (I) are produced by reacting a compound having the formula

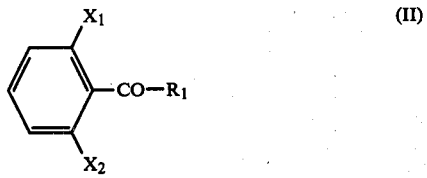
(II)

wherein $X_1$ represents a halogen atom or methyl group; $X_2$ represents hydrogen or halogen atom; $R_1$ represents amino or isocyanate group with a compound having the formula

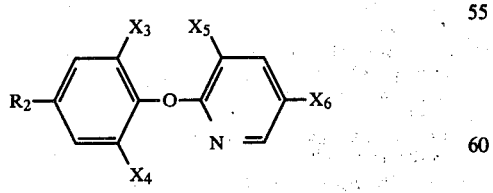

wherein $X_3$ and $X_4$ are the same and different and respectively represent hydrogen or halogen atom; $X_5$ represents hydrogen or halogen atom; $X_6$ represents halogen atom or nitro or trifluoromethyl group; and $R_2$ represents an amino or isocyanate group and $R_2$ is amino group in the case that $R_1$ is isocyanate group, $R_2$ is isocyanate group in the case that $R_1$ is amino group.

More particularly, the compounds having the formula (I) can be produced by the following processes (1) and (2).

(1) The reaction of benzoyl isocyanate having the formula

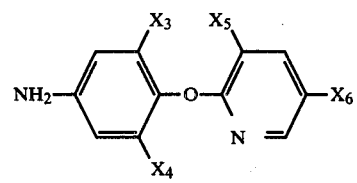

with pyridyloxy aniline having the formula

NH$_2$—⟨structure⟩—O—⟨pyridyl⟩—X$_6$ with X$_3$, X$_4$, X$_5$ (wherein $X_1, X_2, X_3, X_4, X_5$ and $X_6$ are defined above)

(2) The reaction of benzamide having the formula

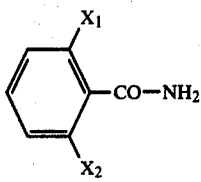

with pyridyloxy phenyl isocyanate having the formula

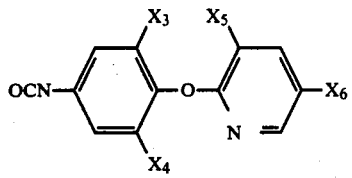

(wherein $X_1$, $X_2$, $X_3$, $X_4$, $X_5$, and $X_6$ are defined above).

The reaction is preferably carried out in the presence of a solvent. Suitable solvents include benzene, toluene, xylene, pyridine etc.

The reaction temperature is usually in a range of 0° to 120° C. and the reaction time is usually in a range of 0.1 to 24 hours. The reaction is preferably carried out at the temperature from 50° C. to a refluxing temperature for 1 to 5 hours.

Certain examples of preparations of the compounds of the present invention will be described.

EXAMPLE 1

Preparation of N-(2-chlorobenzoyl)N'-[3-chloro-4-(3,5-dichloropyridyl-2-oxy)phenyl]urea A solution prepared by dissolving 2.9 g of 3-chloro-4-(3,5-dichloro-pyridyl-2-oxy) aniline in 50 ml of toluene was heated at 80° C. A solution prepared by dissolving 1.8 g of 2-chlorobenzoyl isocyanate in 20 ml of toluene was added dropwise to the former solution under stirring it and the reaction was carried out for 1 hour. After the reaction, the reaction mixture was cooled and the precipitate was filtered and washed with toluene and then with petroleum ether and dried to obtain 3.2 g of N-(2-chlorobenzoyl)N'-[3-chloro-4-(3,5-dichloropyridyl-2-oxy)phenyl]urea (m.p. 225° to 228° C.).

EXAMPLE 2

Preparation of N-(2,6-dichlorobenzoyl)N'-[4-(3,5-dichloropyridyl-2-oxy)phenyl]urea In accordance with the process of Example 1, except using 2.5 g of 4-(3,5-dichloropyridyl-2-oxy)aniline instead of 3-chloro-4-(3,5-dichloropyridyl-2-oxy)aniline and using 2.4 g of 2,6-dichlorobenzoyl isocyanate instead of 2-chlorobenzoyl isocyanate and reacting at 30° C. for 8 hours instead of 80° C. for 1 hour, the process was repeated to obtain 3.8 g of N-(2,6-dichlorobenzoyl)N'-[4-(3,5-dichloropyridyl-2-oxy)phenyl]urea (m.p. 228° to 230° C.).

The compounds of the present invention impart excellent selective insecticidal effect as clearly understood from the following experiments.

EXAMPLE 3

Preparation of N-(2,6-difluorobenzoyl)N'-[4-(3-chloro-5-trifluoromethylpyridyl-2-oxy)phenyl]urea In accordance with the process of Example 1, except using 1.0 g of 4-(3-chloro-5-trifluoromethylpyridyl-2-oxy)anilin instead of 3-chloro-4-(3,5-dichloropyridyl-2-oxy)aniline and using 0.64 g of 2,6-difluorobenzoyl isocyanate instead of 2-chlorobenzoyl isocyanate and reacting at room temperature for 3 hours instead of 80° C. for 1 hour, the process was repeated to obtain 0.5 g of N-(2,6-difluorobenzoyl) N'-[4-(3-chloro-5-trifluoromethylpyridyl-2-oxy)phenyl]urea (m.p. 190° to 192° C.).

EXAMPLE 4

Preparation of N-(2-methylbenzoyl)N'-[4-(5-trifluoromethylpyridyl-2-oxy)phenyl]urea A solution was prepared by dissolving 0.5 g of 4-(5-trifluoromethylpyridyl-2-oxy)aniline in 20 ml of toluene. A solution prepared by dissolving 0.32 g of 2-methylbenzoyl isocyanate in 20 ml of toluene was added dropwise to the former solution under stirring it and the reaction was carried out at room temperature for 1 hour.

After the reaction, the reaction mixture was cooled and the precipitate was filtered and washed with hexane and then recrystallized from ethanol to obtain 0.3 g of N-(2-methylbenzoyl)N'-[4-(5-trifluoromethylpyridyl-2-oxy)phenyl]urea (m.p. 140° to 142° C.).

Most of the conventional insecticides impart quick effect and neurotoxicity and contact toxicity. However, the compounds of the present invention impart the delayed effect that the compounds affect to molting (ecdysis) and metamorphosis of specific insects which orally take the compound with feeds or water whereby the death of the specific insects is caused.

The compounds of the present invention impart remarkable insecticidal effect to larvae of Lepidoptera, Coleoptera, Hymenoptera and Diptera, for example, larvae of the following insects:

diamondback moth (*Plutella xylostella*), common white (*Pieris rapae crucivora*), cabbage armyworm (*Mamesta brassicae*), cabbage looper (*Plusia nigrisigma*), tobacco cutworm (*Prodenia litura*), smoller citrus dog (*Papilio xuthus*), small blackish cochlid (*Seopelodes contracta*), fall webworm (*Hyphantria cunea*), gypsy moth (*Lymantria dispar*), rice stem borer (*Chilo suppressalis*), bollworm (*Heliothis zea*), tobacco budworm (*Heliothis virescens*), bollweevil (*Anthonomus grandis*), confused flour beetle (*Tribolium confusum*), colorado potato beetle (*Leptinotarsa decemlineata*), sawfly (*Neurotoma irdescens*), Culex mosquito (*Culex pipiens pallens*), mosquito (*Culex pipiens molestus*).

The compounds of the present invention do not substantially impart insecticidal effect to adults and are ineffective to natural enemies as predatory insects and impart low toxicity to animals.

When the compounds are used as active ingredients of the insecticidal composition, it is possible to prepare various forms of the compositions such as dust, wettable powder, emulsifiable concentrate, invert emulsion, oil solution, aerosol preparation, etc. with adjuvants as the cases of agricultural compositions. The compositions can be applied with or without diluting them in suitable concentrations.

Suitable adjuvants include powdery carriers such as talc, kaolin, bentonite, diatomaceous earth, silicon dioxide, clay and starch; liquid diluents such as water, xylene, toluene, dimethylsulfoxide, dimethyl formamide, acetonitrile, and alcohol; emulsifiers dispersing agents spreaders etc.

The concentration of the active ingredient in the selective insecticidal composition is usually 5 to 80 wt. % in the case of the oily concentrate; and 0.5 to 30 wt. % in the case of dust; 5 to 60 wt. % in the case of wettable powder.

It is also possible to combine with the other agricultural ingredients such as the other insecticides, miticides, plant growth regulators. Sometimes synergetic effects are found.

The selective insecticides of the present invention are effective for inhibiting various injurious insects and they are usually applied at a concentration of the active ingredients of 5 to 10,000 ppm preferably 20 to 2,000 ppm.

When the active ingredient of the present invention is applied to noxious insects in water the composition having said concentration can be applied to inhibit them, whereby the concentration of the active ingredient in water can be lower than said concentration.

EXPERIMENT 1

The active ingredients were respectively dispersed in water to prepare dispersions having specified concentrations. Leaves of cabbage were dipped into the dispersions for about 10 seconds and taken out and dried under passing air.

A piece of moistened filter paper was put on each Petri dish (diameter 9 cm) and the dried leaves of cabbage were put on the filter paper and larvae of diamondback moth in 2nd or 3rd instar were fed on them and the Petri dishes were covered and kept in constant temperature at 28° C. with lightening. After 8 days from the treatment with the dispersion, the dead larvae were measured and the mortality rates were calculated by the following equation:

$$\text{Mortality rate} = \frac{\text{dead larvae}}{\text{total larvae}} \times 100$$

Table 1

| Compound No. | Mortality rate (%) (concentration) | | Compound No. | Mortality rate (%) (concentration) | |
|---|---|---|---|---|---|
| | 200 ppm | 100 ppm | | 200 ppm | 100 ppm |
| 1 | 100 | 100 | 20 | 100 | 100 |
| 2 | 100 | 100 | 21 | 100 | 100 |
| 3 | 100 | 100 | 22 | 100 | 100 |
| 4 | 100 | 100 | 23 | 100 | 100 |
| 5 | 100 | 100 | 24 | 100 | 100 |
| 6 | 100 | 100 | 25 | 100 | 100 |
| 7 | 100 | 80 | 26 | 100 | 100 |
| 8 | 100 | 100 | 27 | 100 | 100 |
| 9 | 100 | 100 | 28 | 100 | 100 |
| 10 | 100 | 60 | 31 | 100 | 100 |
| 11 | 100 | 80 | 33 | 100 | 100 |
| 12 | 100 | 100 | 34 | 100 | 100 |
| 13 | 100 | 100 | 35 | 100 | 100 |
| 14 | 100 | 100 | 36 | 100 | 100 |
| 15 | 100 | 100 | 38 | 100 | 100 |
| 16 | 100 | 100 | 39 | 100 | 100 |
| 17 | 100 | 100 | 40 | 100 | 100 |
| 18 | 100 | 100 | 41 | 100 | 100 |
| 19 | 80 | 60 | | | |

EXPERIMENT 2

On radish young seedlings grown in unglazed pots, adults of diamondback moth were fed and kept for 24 hours to blow ova. One day later, aqueous dispersions of the active ingredients (500 ppm) were respectively sprayed on the young seedlings to fall drops of the dispersion and dried and kept in glass greenhouse. After 10 days from the treatment with the dispersion, the mortal larvae were measured and the mortality rates were calculated by the equation $$\text{Mortality rate} = \frac{\text{dead larvae}}{\text{total hatched larvae}} \times 100.$$

The results are shown in Table 2.

Table 2:

| Compound No. | Mortality rate (%) |
|---|---|
| 2 | 80 |
| 4 | 100 |
| 6 | 100 |

EXPERIMENT 3

About 20 cc of germinated rice seeds were put into cups (diameter: 9 cm, height: 3 cm) to grow them. When they grew to seedlings having a height of 1 to 2 cm, the aqueous dispersions at specified concentrations were respectively sprayed at a ratio of 2 cc per 1 cup and dried, and larvae of rice stem borer (just hatched) were fed and the cups were covered. After 10 days from the treatment with the dispersion, the dead larvae were measured and the mortality rates were calculated by the equation of Experiment 1. The results are shown in Table 3.

Table 3:

| Compound No. | Mortality rate (%) (concentration) | |
|---|---|---|
| | 200 ppm | 100 ppm |
| 1 | 100 | 100 |
| 2 | 100 | 100 |
| 4 | 100 | 100 |
| 6 | 100 | 100 |
| 11 | 100 | 100 |
| 12 | 100 | 100 |
| 23 | 100 | 100 |
| 24 | 100 | 100 |

EXPERIMENT 4

In a cup (diameter of 9 cm; height of 3 cm), about 20 cc of emerged rice seeds were bred to grow to young seedlings having height of 1.5 to 2 cm and then, 2 cc of each composition having 400 ppm a concentration of each active ingredient was sprayed per 1 cup, and dried, and larvae of rice stem borer in 3rd instar were fed on them and Petri dish was covered. After 10 days from the treatment, the dead larvae were measured and the mortality rates were calculated in accordance with the method of Experiment 1. The results are shown in Table 4.

Table 4:

| Compound No. | Mortality rate (%) |
|---|---|
| 31 | 100 |
| 33 | 100 |
| 34 | 100 |

Table 4:-continued

| Compound No. | Mortality rate (%) |
| --- | --- |
| 36 | 100 |
| 37 | 100 |
| 38 | 100 |
| 39 | 100 |

EXPERIMENT 5

N-(2-chlorobenzoyl)N'-[4-(3,5-dibromopyridyl-2-oxy) phenyl]urea (Compound No. 3) was used to prepare the aqueous dispersions at specified concentrations. The effects of the dispersions to various insects were tested. The mortality rates after 10 days from the treatments were obtained in accordance with the process of Experiment 1.

The results are shown in Table 5.

Table 5:

| Insects | Treatment | Concentration (ppm) | Mortality rate |
| --- | --- | --- | --- |
| cabbage armyworm: 2nd instar larvae (Lepidoptera) | cabbage leaf dipping | 50 | 100 |
| confused flour beetle: 2nd larval instar larvae (Coleoptera) | wheat flour blending | 200 | 100 |
| 1 sp. of sawfly 3rd instar larvae (Hymenoptera) | cherry branch spraying | 250 | 100 |

EXPERIMENT 6

Leaves of azalea were dipped in an aqueous solution of each active ingredient (50 ppm) for 10 seconds, and they were dried in air and charged in a wide mouth glass bottle, and larvae of gypsy moth in 2nd instar were fed on them. The mouth of the bottle was covered with a gauze and was kept in a thermostat constant temperature bath with light at 28° C. After 6 days from the treatment, the dead larvae were measured and the mortality rates were calculated in accordance with the method of Experiment 1. The results are shown in Table 6.

Table 6:

| Compound No. | Mortality rate (%) |
| --- | --- |
| 3 | 100 |
| 13 | 100 |
| 15 | 100 |
| 12 | 100 |
| 20 | 100 |
| 11 | 100 |
| 23 | 100 |
| 24 | 100 |
| 25 | 100 |
| 27 | 100 |
| 28 | 100 |
| 35 | 100 |
| 41 | 100 |

EXPERIMENT 7

Leaves of cabbage were dipped in an aqueous solution of each active ingredient (50 ppm) for 10 seconds, and they were dried in air. A wet filter paper was disposed in each Petri dish (diameter of 9 cm) and each leaf was put on it and larvae of tabacco cutworm in 2nd or 3rd instar were fed and the Petri dish was covered and was kept in a thermostat constant temperature bath with light at 28° C. After 7 days from the treatment, the dead larvae were measured and the mortality rates were calculated in accordance with the method of Experiment 1. The results are shown in Table 7.

Table 7:

| Compound No. | Mortality rate (%) |
| --- | --- |
| 3 | 100 |
| 4 | 100 |
| 13 | 100 |
| 14 | 100 |
| 15 | 100 |
| 12 | 100 |
| 20 | 100 |
| 21 | 100 |
| 24 | 100 |
| 25 | 100 |
| 26 | 100 |
| 33 | 100 |
| 35 | 100 |
| 39 | 100 |

EXPERIMENT 8

In each cup (diameter of 9 cm), about 250 ml of an aqueous solution of each active ingredient (100 ppb) was charged, larvae of mosquito (Culex pipiens molestus) in 3rd instar were charged and the cup was covered and was kept in a thermostat constant temperature bath with light at 28° C. After 10 days from the treatment, the dead larvae were measured and the mortality rates were calculated in accordance with the method of Experiment 1. The results are shown in Table 8.

Table 8:

| Compound No. | Mortality rate (%) |
| --- | --- |
| 3 | 100 |
| 8 | 100 |
| 11 | 100 |
| 12 | 100 |
| 13 | 100 |
| 15 | 100 |
| 20 | 100 |
| 21 | 100 |
| 23 | 100 |
| 24 | 100 |
| 25 | 100 |
| 27 | 100 |
| 28 | 100 |
| 39 | 100 |

Composition 1:

| (a) | N-(2-chlorobenzoyl)N'-[3-chloro-4-(3,5-dichloropyridyl-2-oxy)phenyl]urea | 20 wt. parts |
| --- | --- | --- |
| (b) | Dimethyl sulfoxide | 70 wt. parts |
| (c) | Polyoxyethylenealkylphenyl ether | 10 wt. parts |

The components were uniformly blended to dissolve the ingredient to prepare an emulsifiable concentrate.

Composition 2:

| (a) | N-(2-chlorobenzoyl)N'-[4-(3,5-dichloropyridyl-2-oxy)phenyl]urea | 5 wt. parts |
| --- | --- | --- |
| (b) | Talc | 92 wt. parts |
| (c) | Sodium naphthalene sulfonate | |

-continued

| formaldehyde condensate | 3 wt. parts |

The mixture was pulverized to uniformly mix them to prepare a dust.

Composition 3:

| (a) N-(2,6-dichlorobenzoyl)N'-[4-(3,5-dichloropyridyl-2-oxy) phenyl]urea | 50 wt. parts |
| (b) Jeeklite (fine divided clay) | 45 wt. parts |
| (c) Sodium ligninsulfonate | 5 wt. parts |

The components were pulverized to uniformly mix them to prepare a wettable powder.

Composition 4:

| (a) N-(2,6-difluorobenzoyl)N'-[4-(3-chloro-5-trifluoromethylpyridyl-2-oxy) phenyl] urea | 20 wt. parts |
| (b) N,N-dimethylformamide | 70 wt. parts |
| (c) Polyoxyethylenealkylphenyl ether | 10 wt. parts |

The components were uniformly blended to dissolve the ingredient to prepare an emulsifiable concentrate.

Composition 5:

| (a) N-(2-chlorobenzoyl)N'-[3,5-dichloro-4-(-3-chloro-5-trifluoromethylpyridyl-2-oxy)phenyl]urea | 5 wt. parts |
| (b) Talc | 95 wt. parts |

The mixture was pulverized to uniformly mix them to prepare a dust.

Composition 6:

| (a) N-(2-methylbenzoyl)N'-[3-chloro-4-(3-chloro-5-trifluoromethylpyridyl-2-oxy)phenyl]urea | 5 wt. parts |
| (b) Talc | 95 wt.parts |

The mixture was pulverized to uniformly mix them to prepare a dust.

What is claimed is:

1. N-benzoyl N'-pyridyloxy phenyl urea having the formula

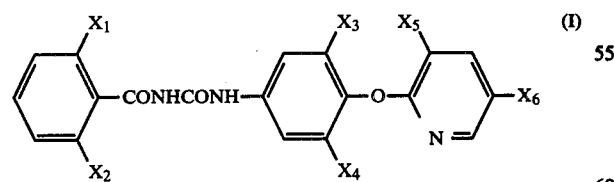

wherein $X_1$ represents a halogen atom or methyl group; $X_2$ represents hydrogen or halogen atom; $X_3$ and $X_4$ respectively represent hydrogen or halogen atom; $X_5$ represents hydrogen or halogen atom; $X_6$ represents a halogen atom or nitro or trifluoromethyl group.

2. N-benzoyl N'-pyridyloxy phenyl urea according to claim 1 which has the formula

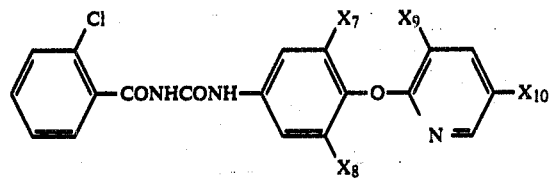

wherein $X_7$ and $X_8$ respectively represent hydrogen or halogen atom; $X_9$ represents hydrogen or halogen atom; $X_{10}$ represents a halogen atom or trifluoromethyl group.

3. N-benzoyl N'-pyridyloxy phenyl urea according to claim 2 which has the formula

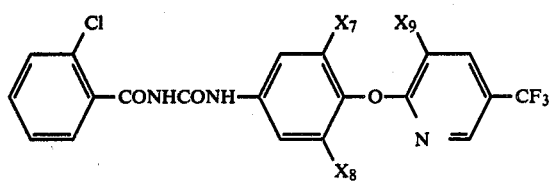

wherein $X_7$, $X_8$ and $X_9$ are defined in claim 2.

4. N-(2-chlorobenzoyl)N'-[4-(3-chloro-5-trifluoromethylpyridyl-2-oxy)phenyl]urea.

5. N-(2-chlorobenzoyl)N'-[3,5-dichloro-4-(5-trifluoromethylpyridyl-2-oxy)phenyl]urea.

6. N-(2-chlorobenzoyl)N'-[3,5-dichloro-4-(3-chloro-5-trifluoromethylpyridyl-2-oxy)phenyl]urea.

7. N-(2-chlorobenzoyl)N'-[3-chloro-4-(3-chloro-5-trifluoromethylpyridyl-2-oxy)phenyl]urea.

8. N-benzoyl N'-pyridyloxy phenyl urea according to claim 1 which has the formula

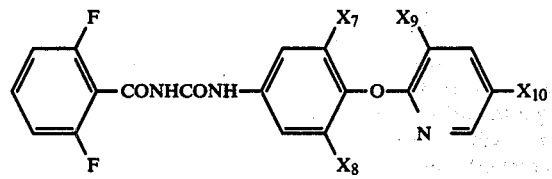

wherein $X_7$ and $X_8$ respectively represent hydrogen or halogen atom; $X_9$ represents hydrogen or halogen atom; $X_{10}$ represents a halogen atom or trifluoromethyl group.

9. N-benzoyl N'-pyridyloxy phenyl urea according to claim 8 which has the formula

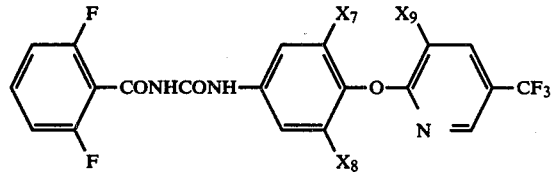

wherein $X_7$, $X_8$ and $X_9$ are defined in claim 8.

10. N-(2,6-difluorobenzoyl)N'-[4-(3-chloro-5-trifluoromethylpyridyl-2-oxy)phenyl]urea.

11. N-(2,6-difluorobenzoyl)N'-[3,5-dichloro-4-(5-trifluoromethylpyridyl-2-oxy)phenyl]urea.

12. N-(2,6-difluorobenzoyl)N'-[3,5-dichloro-4-(3-chloro-5-trifluoromethylpyridyl-2-oxy)phenyl]urea.

13. N-(2,6-difluorobenzoyl)N'-[3-chloro-4-(3-chloro-5-trifluoromethylpyridyl-2-oxy)phenyl]urea.

14. N-benzoyl N'-pyridyl phenyl urea according to claim 1 which has the formula

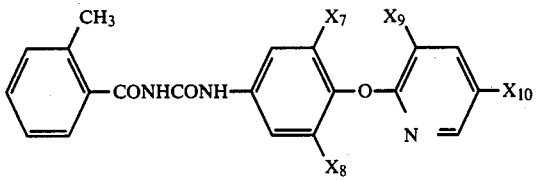

wherein $X_7$ and $X_8$ respectively represent hydrogen or halogen atom; $X_9$ represents hydrogen or halogen atom; $X_{10}$ represents a halogen atom or trifluoromethyl group.

15. N-(2-methylbenzoyl)N'-[3-chloro-4-(3,5-dichloropyridyl-2-oxy)phenyl]urea.

16. N-benzoyl N'-pyridyl phenyl urea according to claim 14 which has the formula

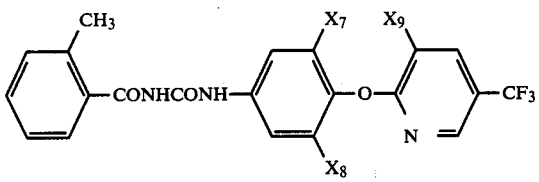

wherein $X_7$, $X_8$ and $X_9$ are defined in claim 14.

17. N-(2-methylbenzoyl)N'-[3-chloro-4-(5-trifluoromethylpyridyl-2-oxy)phenyl]urea.

18. N-(2-methylbenzoyl)N'-[3,5-dichloro-4-(3-chloro-5-trifluoromethylpyridyl-2-oxy)phenyl]urea.

19. N-(2-methylbenzoyl)N'-[4-(3-chloro-5-trifluoromethylpyridyl-2-oxy)phenyl]urea.

20. N-(2-methylbenzoyl)N'-[3-chloro-4-(3-chloro-5-trifluoromethylpyridyl-2-oxy)phenyl]urea.

21. An insecticidal composition which comprises an insecticidally effective amount of a N-benzoyl N'-pyridyloxy phenyl urea having the formula (I) according to claim 1 in admixture with a suitable carrier or adjuvant therefor.

22. An insecticidal composition according to claim 21 which comprises 0.5 to 80 wt. parts of N-benzoyl N'-pyridyloxy phenyl urea having the formula (I) and 20 to 99.5 wt. parts of an agricultural adjuvant.

23. An insecticidal composition according to claim 21 wherein the active ingredient is N-(2-chlorobenzoyl)N'-[4-(3-chloro-5-trifluoromethylpyridyl-2-oxy)phenyl]urea.

24. An insecticidal composition according to claim 21 wherein the active ingredient is N-(2-chlorobenzoyl)N'-[3,5-dichloro-4-(5-trifluoromethylpyridyl-2-oxy)phenyl]urea.

25. An insecticidal composition according to claim 21 wherein the active ingredient is N-(2-chlorobenzoyl)N'-[3,5-dichloro-4-(3-chloro-5-trifluoromethylpyridyl-2-oxy)phenyl]urea.

26. An insecticidal composition according to claim 21 wherein the active ingredient is N-(2-chlorobenzoyl)N'-[3-chloro-4-(3-chloro-5-trifluoromethylpyridyl-2-oxy)phenyl]urea.

27. An insecticidal composition according to claim 21 wherein the active ingredient is N-(2,6-difluorobenzoyl)N'-[4-(3-chloro-5-trifluoromethylpyridyl-2-oxy)phenyl]urea.

28. An insecticidal composition according to claim 21 wherein the active ingredient is N-(2,6-difluorobenzoyl)N'-[3,5-dichloro-4-(5-trifluoromethylpyridyl-2-oxy)phenyl]urea.

29. An insecticidal composition according to claim 21 wherein the active ingredient is N-(2,6-difluorobenzoyl)N'-[3,5-dichloro-4-(3-chloro-5-trifluoromethylpyridyl-2-oxy)phenyl]urea.

30. An insecticidal composition according to claim 21 wherein the active ingredient is N-(2,6-difluorobenzoyl)N'-[3-chloro-4-(3-chloro-5-trifluoromethylpyridyl-2-oxy)phenyl]urea.

31. An insecticidal composition according to claim 21 wherein the active ingredient is N-(2-methylbenzoyl)N'-[4-(3-chloro-5-trifluoromethylpyridyl-2-oxy)phenyl]urea.

32. An insecticidal composition according to claim 21 wherein the active ingredient is N-(2-methylbenzoyl)N'-[3-chloro-4-(3-chloro-5-trifluoromethylpyridyl-2-oxy)phenyl]urea.

* * * * *